United States Patent [19]

Begin et al.

[11] Patent Number: 5,544,693
[45] Date of Patent: Aug. 13, 1996

[54] PROCESS AND APPARATUS FOR MAKING SOLID SAMPLES OF MOLTEN MATERIAL FOR ANALYSIS OR THE LIKE

[75] Inventors: Pierre Begin; Denis Choquette; Rejean Tremblay, all of Quebec, Canada

[73] Assignee: Alcan International Limited, Montreal, Canada

[21] Appl. No.: 355,596

[22] Filed: Dec. 14, 1994

[51] Int. Cl.$^6$ .................... B22D 2/00; G01N 1/14
[52] U.S. Cl. .................... 164/4.1; 164/150.1; 73/864.54; 73/DIG. 9
[58] Field of Search .................... 164/4.1, 150.1; 73/864.53, 864.54, 864.55, 864.58, DIG. 9

[56] References Cited

U.S. PATENT DOCUMENTS

| | | | |
|---|---|---|---|
| 3,974,698 | 8/1976 | Scott, Jr. | 73/425.6 |
| 4,007,641 | 2/1977 | Kelsey | 73/425.6 |
| 4,179,931 | 12/1979 | Moriya | 73/425.6 |
| 4,428,245 | 1/1984 | Nakamura et al. | 73/864.52 |

FOREIGN PATENT DOCUMENTS 2086040  5/1982  United Kingdom.

OTHER PUBLICATIONS

Vieth et al "Analysis of High–Purity Gallium by high–resolution glow discharge . . . " Analytical Chemistry, 1992, 64, pp. 2958–2964.

Primary Examiner—Kuang Y. Lin
Attorney, Agent, or Firm—Cooper & Dunham LLP

[57] ABSTRACT

A method and apparatus for sampling molten materials, such as metals and molten salt mixtures, for analysis by spectroscopy or other means involves forming small, preferably "pin-like" samples by quickly drawing an amount of the molten material from a molten pool into a tubular element, referred to as a pipette, forming an elongated mould having a ratio of length to thickness of at least 2:1, allowing the molten material to cool and solidify in the pipette and then removing the solid sample from the pipette. The pipette is made of a material of high total heat capacity heat relative to the heat capacity of the sample material, i.e. in the ratio of 10-450:1, so that heat is quickly withdrawn from the molten material, allowing it to solidify within about 2 seconds or less. The sample of material is quickly withdrawn from the pool into the pipette by instantaneously creating a vacuum in the interior of the pipette, preferably by means of a syringe-like device or a rod snugly slidable within the internal bore of the pipette. The rapid cooling of the sample avoids lack of homogeneity within the solidified sample and the small size and elongated shape of the sample mean that all of the sample can be analyzed for greater accuracy and the sample easily and rapidly dissolves in solvents or reactants.

12 Claims, 2 Drawing Sheets

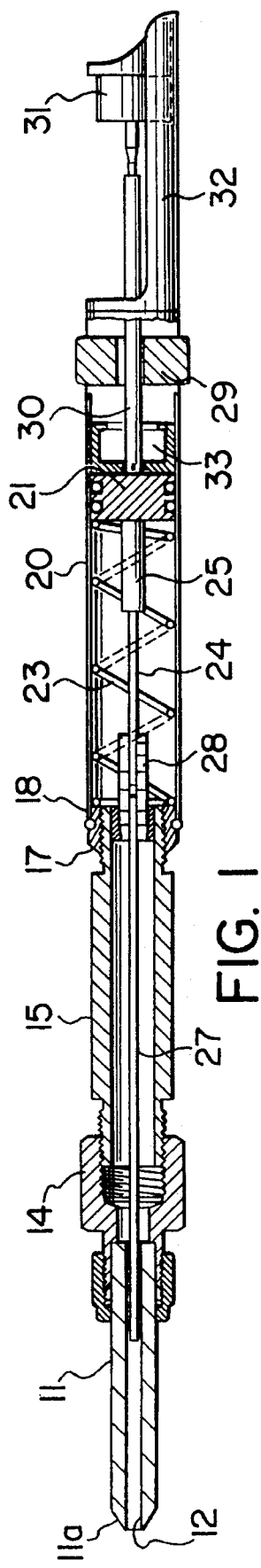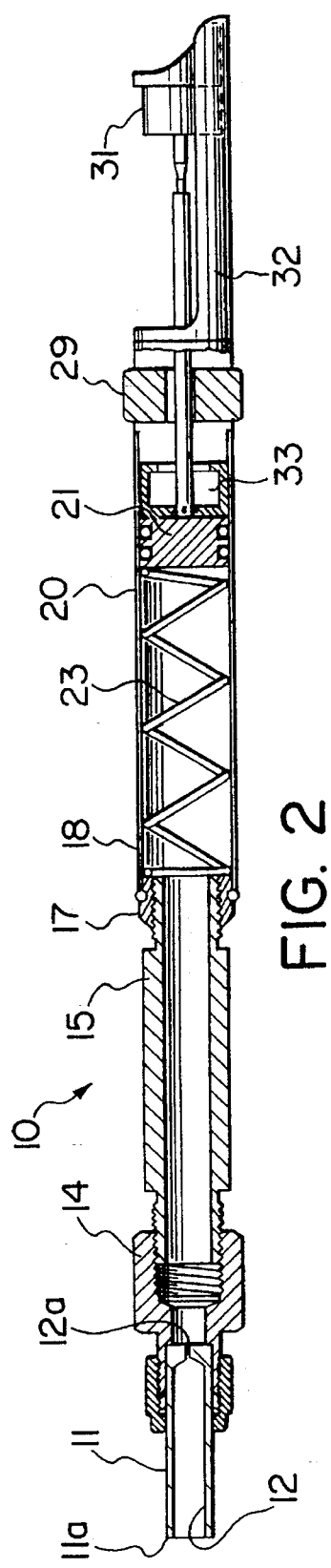

PROCESS AND APPARATUS FOR MAKING SOLID SAMPLES OF MOLTEN MATERIAL FOR ANALYSIS OR THE LIKE

BACKGROUND OF THE INVENTION

I. Field of the Invention

This invention relates to procedures for sampling molten materials, e.g. molten metals and salts, for purposes such as analysis or testing. More particularly, the invention relates to such procedures intended for obtaining small samples that are representative in terms of the composition of the bulk of the molten material.

II. Description of the Prior Art

It is often important in many industries to test the compositions of pools of molten materials during manufacturing processes, e.g. for process control or for certification of materials sold to customers. For this purpose, small samples of the materials are usually extracted and allowed to solidify and then the solids are analyzed directly, or after being dissolved in suitable solvents or liquid reactants, by techniques such as spectroscopy. Many such techniques test only very small volumes of the sampled material, so if the sample actually tested is not fully representative of the composition of the bulk material, the test results may be inaccurate. For example, optical emission spectroscopy uses a spark source to volatilize a small surface portion of a solid sample and the spectrum of the volatilized material is then determined. Similarly, inductively coupled emission spectroscopy uses a plasma to vaporize and excite a solution containing a metal sample dissolved acidic solution at a concentration of about 1 to 2%.

Unfortunately, it is extremely difficult in practice to obtain a solid sample from an homogenous pool of molten material that is itself fully homogenous and accurately representative of the bulk material. This is because there is a significant segregation of the constituent elements when large quantities of many molten mixtures are allowed to solidify relatively slowly. This is particularly true when the molten material is a mixture of two or more components, e.g. alloys or salt mixtures, however, inhomogeneities can also materialize when materials that are considered to be single components are cooled. This is because commercial industrially-produced metals and salts are rarely pure and are thus rarely single-components systems. Moreover, even relatively pure single component systems may cool to form inhomogeneous crystallographic regions, e.g. regions having crystals of different sizes or crystal structure due to differential rates of cooling. Such metals may therefore not be homogenous to the metallographer or crystallographer, even though samples may be homogeneous from the bulk chemical perspective.

In conventional sampling techniques involving the pouring of a relatively large volume of the molten material into a cool mould to form a disc-like or cylindrical sample typically weighing 25 to 160 g or more (when the material is a metal), each alloying or constituent element present in the molten material tends to migrate at a different distinctive rate from the colder outside part of the sample to the warmer inner part. This causes quite significant concentration contours or profiles in the sample, when it is fully solidified. The differential distribution of elements along the lengths and widths of these samples makes it an extreme challenge to select an area of a sample that should be analyzed to ensure representative results. To ensure the highest accuracy, it would be necessary to analyze the entire sample, but this would involve vaporizing or dissolving the total sample weight. Clearly, vaporization of a large sample cannot be achieved using rapid or economic means. Dissolving an entire sample, in the case of a metal, involves machining the sample to reduce it to small chips or turnings, and then dissolving the entire mass in acid or the like. This is an extremely slow and expensive process.

This problem could be reduced if samples of the molten material could be extracted and cooled fast enough to avoid significant partitioning of the melt, but molten materials, and particularly molten metals and salts, are difficult to handle quickly and accurately because of their problematic fluid properties, high temperatures and high latent heats of solidification that tend to slow cooling times.

Various sampling devices are known for removing test samples of molten materials, but they either produce samples that are too large for modern testing methods, and are hence slow to cool, or they are cumbersome and inefficient. Some of these known test devices are discussed below as typical examples of what is already known.

Edward J. Kelsey in U.S. Pat. 4,007,641 issued on Feb. 15, 1977 describes a molten metal sampler having a chamber that can be evacuated and that is adapted to hold the vacuum until the sampler is used. When the sampler is contacted by molten metal, a seal holding the vacuum disintegrates to permit passage of molten metal into the chamber where the metal cool and solidifies to form a large disc or pin shape. However, the large sample is allowed to cool naturally and so the homogeneity of the sample is unlikely to be acceptable. Moreover, the device is inconvenient to use because it has to be evacuated using some kind of pumping device and then sealed before it can be used.

Kazuo Moriya in U.S. Pat. 4,179,931 discloses a similar concept in which molten metal is drawn into an evacuated insulated paperboard cartridge through an elongated fill tube secured to the side of the cartridge. A separate cumbersome pumping device is required to evacuate the cartridge and natural cooling of the sample takes place.

In British patent application 2 086 040 A published on May 6, 1982, Cottam et al. disclose a molten metal sampler consisting of a uniform bore silica tube open at both ends and surrounded along its length by a sleeve of molten refractory. The sample is obtained by immersing one end of the tube into the melt for a period of time (five or six seconds) sufficient to allow the molten material to freeze in the bore. The tube is extracted and water-quenched and then the sample, in the form of relatively thin rod or pin, is retrieved by breaking the tube. Even though the samples are quite small, cooling and solidification may be slow enough to produce non-homogenous samples.

Finally, Vieth et al. in Analytical Chemistry, 1992, 64, 2958–2964 discloses a procedure to convert molten gallium into solidified pins for analysis. The procedure involves inserting a small TEFLON® tube of 2.5 mm outside diameter into the melt, drawing the melt up into the tube by undisclosed means, removing the filled tube, quenching the tube and solidifying the contents by plunging the tube into a refrigerant such as liquid nitrogen. This procedure is clearly inconvenient because of the need for specialized refrigerant and, moreover, since solidification may commence before the tube is plunged into the refrigerant, the homogeneity of the resulting sample may not be acceptable.

There is accordingly, a need for an improved method and apparatus for sampling molten material such as metal alloy or salt mixtures.

SUMMARY OF THE INVENTION

An object of this invention is to facilitate sampling of molten materials for the purpose of analysis or testing.

Another object of the invention is to enable the production of small solid samples of molten materials that are quite homogeneous and representative of the bulk material from which they are extracted.

Another object of the invention is to permit sampling of molten materials without causing undue separation of components during the sampling procedure.

Yet another object of at least preferred forms of the invention is to produce small samples in a shape that facilitates dissolving of the entire solid test sample in a solvent or liquid reactant or that makes complete vaporization of the solid material commercially feasible.

According to the invention, there is provided a process of obtaining an homogeneous solid sample suitable for analysis from a molten pool of a material having a particular heat capacity, comprising: providing a tubular element having an internal bore forming a mould for a sample of said molten material, said mould having a length and maximum thickness defining an elongated shape such that a ratio of said length to said maximum thickness of said shape is at least 2:1; rapidly drawing an amount of said molten material from said pool into said tubular element to fill said mould; conducting heat from said sample at a rate fast enough to solidify said sample in said mould in a period of two seconds or less from commencement of withdrawal of said sample from said molten pool, said rate of heat conduction being assured by choosing a substance for said tubular element that has a heat capacity such that the ratio of the heat capacity of said sample to the heat capacity of said substance is within the range of 1:10 to 1:450; and removing said solidified sample from said mould.

According to another aspect of the invention, there is provided Sampling apparatus for producing a solid sample suitable for analysis from a molten pool of a material having a particular heat capacity, comprising: a tubular element having an internal bore opening at a tip of said element and forming a mould for a sample of said molten material, said mould having a length and maximum thickness defining an elongated shape, with the ratio of said length to said maximum thickness being at least 2:1, said tubular element being made of a substance having a heat capacity such that the ratio of the heat capacity of said material to the heat capacity of said substance is in the range of 1:10 to 1:450; and a device for drawing molten material into said bore through said opening in said tip from a pool of said molten material to fill said mould sufficiently rapidly to permit filling and solidification of said sample in said mould within a period of two seconds or less of commencement of withdrawal of the material from said molten pool.

By rapidly drawing the molten material into a tubular element defining a mould having an elongated shape and having a high heat capacity, the molten material can be sampled and solidified so rapidly that inhomogeneities have little chance to form in the sample. Moreover, relatively small solid samples can be produced in shapes that facilitate analytical techniques.

The present invention has the advantage of making it possible to produce solid samples of varying sizes that are nevertheless quite homogeneous. The samples can be used for the type of analytical techniques that consume a very small part of the sample or alternatively, when made suitably small, for those techniques which consume the entire sample by vaporization or solubilization. This is made possible by the ability of the invention to manipulate small quantities of test material while producing solid samples of good homogeneity.

It is important in the present invention to mould the sample into an extended elongated shape because heat can quickly disperse from the interior of a sample shaped in this way since all parts of the interior are close to an external surface. While the ratio of length to maximum thickness should be at least 2:1, the ratio is in fact preferably much larger, e.g. at least 10:1. Ideally, the sample is moulded into a cylindrical shape because it is not only easy to produce a tubular element having a cylindrical internal bore, but also because a cylindrical shape is good for heat dispersion from the interior. When the shape of the sample is made long and cylindrical (pin-like), the maximum thickness used in the above ratio is of course the diameter of the circular cross-section of the cylinder. The pin may, however, be made in other shapes, such as plate-like or blade-like shapes, or may be of polygonal cross-section. In such cases, the maximum width used for the ratio mentioned above, is the maximum cross-sectional dimension of the shape.

The sample may be made in virtually any size suitable for sampling purposes, but should preferably be no larger than required for the type of analysis to be employed. Most preferably, the samples are made in a pin-like shape less than about 5 mm in diameter and less than about 5 cm in length.

Another way in which the present invention ensures rapid cooling of the sample is to make the tubular element out of a substance of high total heat capacity compared to the heat capacity of the molten material, as already mentioned above. This ensures that the tubular element acts as a heat sink to rapidly absorb all the heat released on complete solidification of the sample.

The choice of substance for the tubular element (in practice referred to as a "pipette") depends of course on the identity of the material to be sampled in order to provide the required ratio of heat capacities, but for most molten materials, a pipette made of a substance have a room temperature specific heat of at least 0.7 J/g K and a thermal conductivity of at least 3 W m$^{-1}$K$^{-1}$ is suitable in order to provide an effective heat capacity.

As noted above, the molten sample must be drawn rapidly into the mould defined by the interior of the pipette. The rate of withdrawal of the molten material from the pool should preferably be so rapid that filling of the mould can be achieved in one second or less, and more preferably one half second or less. A preferred way to achieve this rapid withdrawal is to create a virtually instantaneous vacuum in the interior of the pipette once the tip of the pipette has been immersed in the molten pool. This can be achieved, for example, by rapidly moving a piston in a cylinder to create a vacuum. The cylinder may be the pipette itself or a larger cylinder communicating with the pipette. The piston may therefore be a rod inserted into the internal bore of the pipette, that is then withdrawn rapidly from the internal bore, or a conventional piston slidable in the larger cylinder communicating with the internal bore. In fact, both means of creating a vacuum may be present, i.e. a combination of a rod in the internal bore and a piston in a larger cylinder communicating with the internal bore, both the rod and piston being moved in unison.

The rapid movement of the piston required to create a vacuum virtually instantaneously can be brought about by spring loading the piston, forcing the piston against the spring to a starting position, restraining the piston in the starting position and then releasing the restraint when the tip has been immersed in the molten pool. The piston may be forced into the starting position by hand, or by means of a hydraulic, pneumatic or electromechanical pushing device. A manually operable device has the advantage that it can be made quite small and portable and can be operated reliably. The use of a piston and cylinder arrangement attached to (or forming part of) the pipette has the advantage that the vacuum is generated at the site of sampling and is thus not created off-site by separate vacuum pumps, requiring transport of a container under vacuum.

By using these criteria, a sample of the molten material can be caused to cool so rapidly that significant separation of the constituent components is avoided, thus providing an homogeneous sample suitable for analysis in part or in its entirety.

It should be noted that the present invention can be used to minimize or avoid inhomogeneities of both multi-component mixtures and relatively pure single component systems.

BRIEF DESCRIPTION OF THE DRAWINGS

FIG. 1 is a cross-section of a sampling device according to one preferred form of the present invention;

FIG. 2 is a view similar to FIG. 1 of an alternative preferred embodiment of the sampling device of the present invention.

DETAILED DESCRIPTION OF THE PREFERRED EMBODIMENTS

Figure 3:
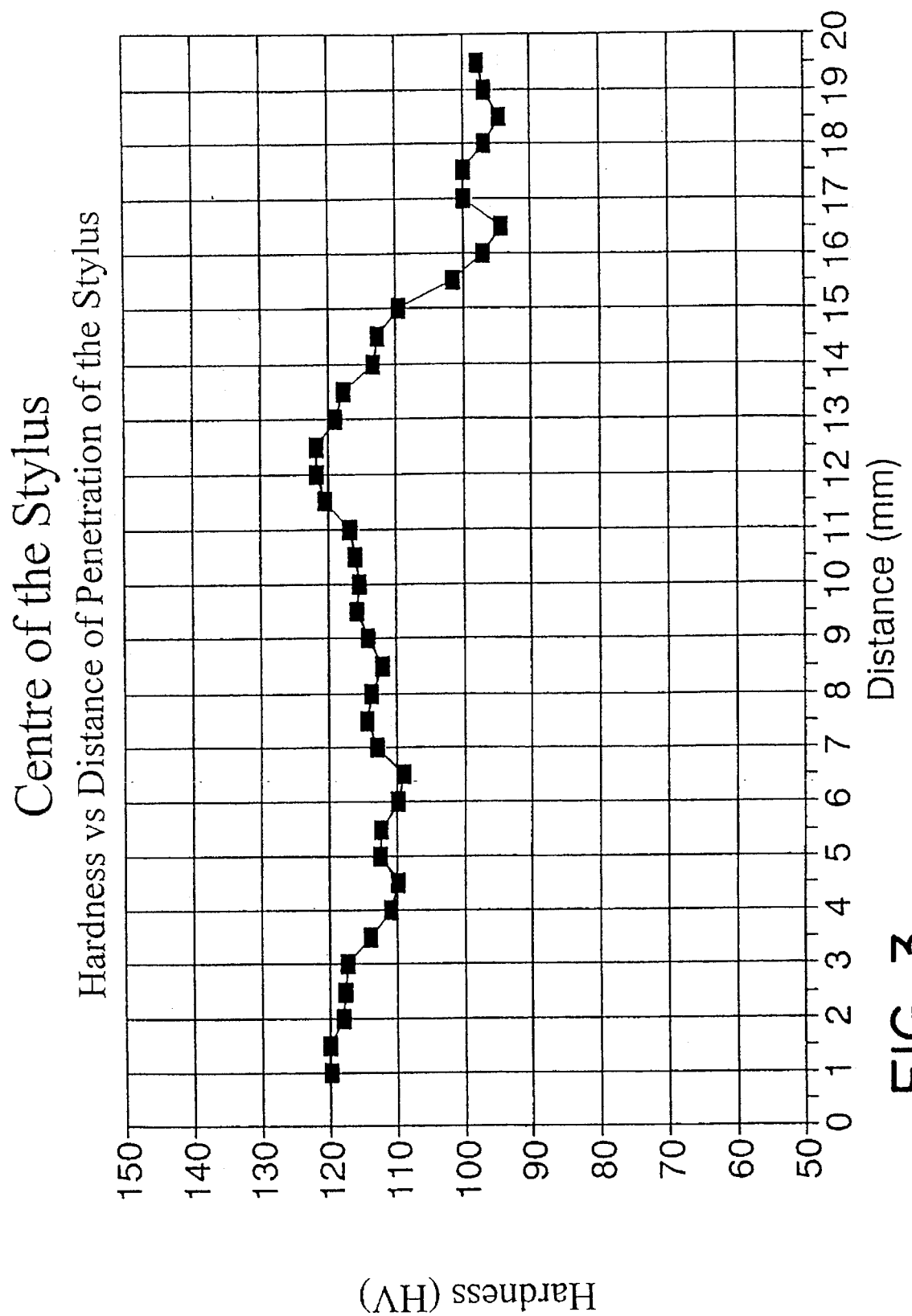
FIG. 3 is a graph showing results obtained in Example 1 below.

A sampling apparatus 10 according to a preferred form of the invention is shown in longitudinal cross-section in FIG. 1. At one end, the apparatus has a tubular element 11 of circular cross-section, referred to hereinafter as a pipette, provided with a longitudinal narrow internal bore 12 also of circular cross-section and of constant diameter throughout the length of the pipette. At the tip of the pipette, the bore 12 is open to the exterior and the pipette is bevelled slightly at its periphery, as shown. The pipette is made of a substance of high thermal conductivity and high specific heat giving it a high total heat capacity. Suitable substances for the pipette include carbon, graphite, graphitized carbon, carbon fibre-reinforced solids made from these materials, and other non-metals, e.g. boron nitride. The substance is chosen to provide a total heat capacity relative to the total heat capacity of the material to be sampled in the stated range of 10–450:1.

When aluminum or aluminum alloy is to be sampled, as well as many other materials, the preferred substance for the pipette is graphite or carbon. The properties of carbon and graphite are as follows:

|  | Carbon | Graphite |
|---|---|---|
| Specific Heat J/g K | 1.0 |  |
| @ Room Temperature |  | 0.71 |
| @ 538° C. |  | 1.63 |
| @ 1093° C. |  | 1.95 |
| Thermal Conductivity $W\ m^{-1}K^{-1}$ | 3–5 | 150–160 |

Graphite is preferred because carbon is more difficult to fabricate.

The internal bore 12 defines a mould for the molten material drawn into the pipette and the part of the bore intended to form the mould has a length to diameter ratio of at least 2:1, and preferably at least 10:1.

Although not shown in the drawings, the pipette may if desired be provided with an outer sleeve or coating of a heat-insulating material, at least adjacent to the tip. Suitable insulating materials for this purpose include calcium silicate refractory board material, e.g. PYROTHERM®-B-3, or boron nitride applied as a paint from a dispersion of particles in a suitable carrier. The insulation is provided to reduce the tendency of molten material from the pool to solidify on the exterior of the pipette at the tip 11a, thus affecting the size and shape of the sample and making extraction of the solidified sample more difficult.

At the inner end of the pipette, a connector 14, preferably made of brass (e.g. SWAGELOK® fitting B-400-7-4) joins the pipette axially to one end of a hollow tubular union 15, also preferably made of brass(e.g. CAJON® model B-4-HLM-3,00). A second connector 17 attaches the opposite end of the union 15 to a cylindrical barrel 18 of a spring-loaded syringe device 20. A particularly suitable syringe for this purpose is the "Vacuum Desoldering Tool" made by Archer (Catalogue number 64-2098A), sold by Tandy Corporation ("Radio Shack"®). The syringe has a piston 21, slidably installed within the barrel 18, that is urged towards the end of the syringe opposite to the union 15 by a coil spring 23 seated against both the inner end of the second connector 17 and the underside of the piston 21. A narrow rod 24 is attached to the inner side of the piston 21 via a connector 25 and extends axially through the barrel 18. At its extreme end, the rod 24 is rigidly attached by means of a coupler 28 (preferably made of stainless steel) to a narrow rod 27 capable of extending to the outermost tip 11a of the pipette 11 through the bore 12, the outer diameter of the rod 27 being sufficiently similar to the inner diameter of the bore 11 that the rod 27 slides snugly in the bore and acts as a piston within the cylinder formed by the pipette. The material of the rod 27 is preferably identical or similar to the material of the pipette itself. When the rod 27 is made of graphite, it has been found convenient to use "leads" from mechanical pencils as the rods 27 (e.g. STAEDTLER® leads) when the internal bore 12 is of suitable diameter, otherwise the rod can be machined from a larger piece of graphite.

At the end remote from the pipette, the internal piston 21 is attached to a second narrow rod 30 extending from the barrel 18 past a detent mechanism 29 to an external plunger 31 mounted within a guide 32 for manual operation by the user. To acquire a sample, the user first depresses the external plunger 31 within the guide 32 against the force of the spring 23 so that the internal plunger moves down the barrel 18 and the rod 27 is pushed through the bore 12 to the end of the pipette 11. The piston 21 is held in this "cocked" position against the spring force by the detent mechanism 29. The tip 11a of the pipette is then immersed in a pool of the molten material to be sampled, and the restraining force on the piston 21 is instantaneously removed by manual triggering of the detent mechanism 29, whereupon the internal piston 21 is forced rapidly along the barrel 18, withdrawing the rod 27 to the opposite end of the pipette and creating a sudden vacuum both in the internal bore 12 and in the barrel 18 communicating with the bore 12. The internal bore 12 rapidly fills with a sample of the molten material from the pool, thus filling the mould defined by an end section of the internal bore. The pipette is then quickly withdrawn from the pool to reduce the possibility of molten material solidifying on the outer surface of the tip 11a. Most preferably, the tip should be withdrawn within about 2 seconds or less from the initial immersion for this reason. The sample in the bore 12 quickly cools and solidifies because of its contact with the substance of the pipette that withdraws the heat from the sample and absorbs the heat of solidification. Once solidified, the sample can be ejected from the pipette by again depressing the external plunger 31 to force the rod 27 through the bore 12.

The length of the sample can be controlled by varying the length of travel of the rod 27 in the bore 12. This in turn can be controlled by means of a travel-limiting spacer 33 positioned between the internal piston 21 and the end cap 29. By replacing one such spacer by another of different thickness, the length of the sample can thus be varied.

As explained earlier the heat capacity of the pipette and the material to be sample must fall within the range of 10–450:1. For greater convenience, for any given combination of sample material and substance of the pipette, this ratio can be expressed as a ratio of the diameter of the internal bore 12 to the outer diameter of the pipette 11. When the pipette is made of graphite and the material to be sampled is aluminum or an aluminum alloy, the diameter of the bore 12 and the outer diameter of the pipette 11 should have a ratio falling within the range of 0.3–2:9 and the length of the pipette is preferably sufficient for it to hold an amount of material in the bore 12 corresponding to a sample weight of 1.5 g or less. The ratio of diameters is determined according to the following calculations.

The total heat capacity of a material may be considered to be its:

volume×specific gravity×room temperature specific heat

For cylindrical shapes of unit length, the above equation can be expressed as:

$$\pi \left( \frac{d}{2} \right)^2 \times \text{specific gravity} \times \text{room temperature specific heat}$$

For the case of aluminum in a graphite pipette, the specific gravity and the specific heats are:

|  | Al | Graphite |
|---|---|---|
| Specific Gravity (g/cc) | 2.70 | 1.70 |
| Specific Heat (cal/g deg) | 0.215 | 0.170 |

A. In the case where the ratio of the total heat capacities is 1:10

10×Heat Capacity of Al=Heat Capacity of Graphite

If the diameter of the Al sample is "d" and the outer diameter of the graphite pipette is "dp", the above equation can be expressed as $$10 \times \pi \left( \frac{d}{2} \right)^2 \times 2.70 \times 0.215 =$$

$$\pi \left[ \left( \frac{dp}{2} \right)^2 - \left( \frac{d}{2} \right)^2 \right] \times 1.70 \times 0.170$$

$1.45\ d^2 = 0.0723\ dp^2 - 0.0723\ d^2$
$1.52\ d^2 = 0.0723\ dp^2$
$21\ d^2 = dp^2$
$4.5\ d = dp$

Thus the ratio of diameters is 1:4.5 or 2:9.

B. In the case where the ratio is 1:450

$$450 \times \pi \left( \frac{d}{2} \right)^2 \times 2.70 \times 0.215 =$$

$$\pi \left[ \left( \frac{dp}{2} \right)^2 - \left( \frac{d}{2} \right)^2 \right] \times 1.70 \times 0.170$$

$65.30\ d^2 = 0.0723\ dp^2 - 0.0723\ d^2$
$65.37\ d^2 = 0.0723\ dp^2$
$904.15\ d^2 = dp^2$
$30.07\ d = dp$ or the ratio of diameters is 1:30.07 or 0.3:9.

Higher ratios, e.g. 4–5:9, do not provide sufficiently rapid cooling rates of the metal, and lower ratios, e.g. 0.2:9, may result in the metal freezing in the bore before the bore is completely full.

For other combinations of material to be sampled and substances used for the pipette, the preferred ratios of diameters will be different, but they can be calculated in a similar way, for example as follows:

The range of diameters must respect the range of Heat Capacities:

Heat capacity metal=1/10 to 1/450 Heat capacity of pipette.

For Lead and Graphite:

Specific Gravity of lead is 11.34 g/cc
Specific Heat of lead is 0.038 cal/g.deg
Thus, for a pin diameter of 2mm and a ratio of Heat Capacity of 1:10, the outer diameter of the pipette must be:

Lead Pin = 1/10 Graphite Pipette
Volume × 11.34 × 0.038 = 1/10 vol. × 1.70 × 0.170
$dPb = 2$ mm, $dp = ?$ $$\pi \left( \frac{dPb}{2} \right)^2 \times 11.34 \times 0.038 =$$

$$\frac{1}{10} \pi \left[ \left( \frac{dp}{2} \right)^2 - \left( \frac{dPb}{2} \right)^2 \right] \times 1.70 \times 0.170$$

$$\frac{10 \times 11.34 \times 0.038}{1.70 \times 0.170} = \left( \frac{dp}{2} \right)^2 - 1$$

$$14.9 = \left( \frac{dp}{2} \right)^2 - 1$$

$15.9 \times 4 = (dp)^2$
$dp = 7.97$ i.e. 8

Thus the outer diameter of the pipette is 8.

While the pipette 11 preferably has a circular cylindrical outer wall, so that the diameter used in the above ratio is clear, other shapes may be employed, in which case the "diameter of the pipette" used in the above ratio is the diameter of a theoretical circle that would hold the same area of solid material as the actual cross-sectional shape of the pipette. This can be calculated as the ratio of areas for unit length.

The effective length of the pipette may be varied at will, but lengths in the range of 1 to 50 mm are preferred in most cases. For metals and molten salt mixtures, these lengths give samples weighing between 20 mg and 0.8 g. Larger sample weights can be obtained either by increasing the length of the pipette or by increasing the diameter of the bore 12 (while maintaining the stated ratio); for example, for metals and salt mixtures, samples weighing 1.5 g can be obtained with a bore of 4.2 mm in diameter and 40 mm long. In contrast, to make a sample of aluminum alloy weighing 1 g, the graphite piston should have diameter of 3 mm and a stroke of 52 mm. Diameters of less than 2 mm are used to make smaller weight samples.

The tubular union 15 serves as a heat sink to provide for a rapid dissipation of the heat contained in the molten material in the pipette and to provide and maintain the alignment between the rod 27 and the bore 12 of the pipette 11. The use of brass as the material of the union 15 helps with this heat dissipation as does the length of the union, which should preferably be in the range of 6 to 20 cm.

An alternative embodiment of a sampling device is shown in FIG. 2. This device is similar to the device of FIG. 1, except that it is designed to produce samples having a reduced diameter at one end to facilitate the insertion of the sample into a conveying mechanism or analyzing device. The internal bore 12 in the pipette 11 is made by machining the bore such that the diameter decreases, for example, from a nominal 3 mm to 0.25 mm (bore 12a) at the inner end of the pipette. To make very small samples, the entire length of the bore can be reduced to 0.25 mm or less. The apparatus of this embodiment does not have the rod 27, coupler 28, rod 24 and connector 25 of the apparatus of FIG. 1. Instead, the apparatus of FIG. 2 relies on the piston 21 moving in the barrel 18 to create an instantaneous vacuum in the barrel 18 and, since the barrel communicates with the internal bore 12, also in the internal bore of the pipette.

With a diameter of 0.25 mm, a sample of aluminum weighing 0.1 mg will have a length of about 7 mm. When samples of such a small size are produced, the solid sample cannot be ejected from the bore of the pipette by pushing (and anyway there is no rod 27 for doing this, unlike the apparatus of FIG. 1). Instead, after each sampling operation, the pipette must be removed from the apparatus and the pipette walls broken into small pieces to recover the sample.

The apparatus of the invention may be provided with a variety of pipettes of different dimensions and substances to suit particular molten materials to be sampled and different analytical techniques to be employed.

The invention is illustrated in further detail with reference to the following Examples, which are not intended too limit the scope of the present invention.

EXAMPLE 1

Microhardness Test

A pin was made from aluminum alloy AA 7010, whose nominal composition was: Si 0.12; Fe 0.15, Cu 1.5–2.0, Mn 0.10, Mg 2.1–2.6, Cr 0.05, Ni 0.05, Zn 5.7–6.7, Zr 0.10–0.16, and other unavoidable impurities totalling 0.15%. The pin was 2 mm in diameter and 20 mm long. The pin was mounted in bakelite and cut longitudinally, then polished. The microhardness in the centre of the pin was measured every 0.5 mm along its length, by a Vickers Hardness Testing instrument employing a penetrating stylus, which gave results in HV units.

The results are shown in FIG. 3 of the accompanying drawings. The values found were between 120 and 95 HV units, much higher than the 30 HV units found in the usual sample, indicating a very fine crystal structure. The relatively small variation between 120 and 95 HV units also indicate a high degree of homogeneity in the crystal structure throughout the length of the pin.

EXAMPLE 2

Spectrographic Analysis

A pin was made from alloy AA 2024, whose nominal composition was Cu 3.8–4.9, Mg 1.2–1.8, Mn 0.3–0.9 along with Fe, Si and Zn and other unavoidable impurities. The pin was 2 mm in diameter and 25 mm long. It was analyzed by optical emission spectroscopy, every 2 mm along its length, from 22 to 8 mm from its end. The remaining length could not be analyzed because this was held in the spark stand of the instrument.

The results are shown in Table I below. The results for the alloying elements Cu, Mg, and Mn do not show any decreasing or increasing trend in the concentration down the length of the pin, indicating that there is segregation. Furthermore the coefficient of variation of the results along the length was 1.9% or better, which is equal or better than that observed when the conventional disc samples are analyzed by optical emission spectroscopy.

TABLE I

RESULTS OF HOMOGENEITY TEST AA 2024

| Length Position Analyzed (mm) | Cu | Fe | Mg | Mn | Si | zn |
|---|---|---|---|---|---|---|
| 22–20 | 4.25 | 0.185 | 1.38 | 0.617 | 0.131 | 0.039 |
| 18–16 | 4.52 | 0.182 | 1.37 | 0.620 | 0.128 | 0.040 |
| 14–12 | 4.27 | 0.188 | 1.38 | 0.621 | 0.132 | 0.041 |
| 10–8 | 4.40 | 0.186 | 1.40 | 0.623 | 0.134 | 0.040 |
| Avg. | 4.34 | 0.185 | 1.38 | 0.620 | 0.131 | 0.040 |
| Std. Devn | 0.074 | 0.0021 | 0.011 | 0.0022 | 0.0019 | 0.00075 |
| C of V | 1.7 | 1.2 | 0.78 | 0.35 | 1.4 | 1.9 |

While preferred embodiments of the invention have been described in detail above, it will be appreciated by persons skilled in the art, after reading this disclosure, that various modifications and alterations will be possible without departing from the spirit and scope of the invention.

What we claim is:

1. A process of obtaining an homogeneous solid sample suitable for analysis from a pool of a molten material having a particular heat capacity, comprising:

providing a tubular element having an internal bore forming a mould for a sample of said molten material, said mould having a length and maximum thickness defining an elongated shape such that a ratio of said length to said maximum thickness of said shape is at least 2:1;

rapidly drawing an amount of said molten material from said pool into said tubular element to fill said mould;

conducting heat from said sample at a rate fast enough to solidify said sample in said mould in a period of two seconds or less from commencement of withdrawal of said sample from said molten pool, said rate of heat conduction being assured by choosing a substance for said tubular element that has a heat capacity such that the ratio of the heat capacity of said sample to the heat capacity of said substance is within the range of 1:10 to 1:450; and removing said solidified sample from said mould.

2. A process according to claim 1 which involves employing a tubular element forming a mould defining a shape in which said ratio of said length to said maximum thickness is at least 10:1.

3. A process according to claim 1 wherein said sample is drawn into said elongated tubular element by submerging a tip of said element, having an opening to said internal bore, into said pool and substantially instantaneously creating a vacuum inside said internal bore.

4. A process according to claim 3 wherein said vacuum is created inside said tubular element by substantially instantaneously moving a piston in a gas-tight cylinder communicating with said internal bore.

5. A process according to claim 3 wherein said vacuum is created inside said tubular element by positioning a rod in said bore to act as a piston, and substantially instantaneously moving said rod through said bore away from said opening in said tip.

6. A process according to claim 5 wherein said sample is removed from said mould after solidification by pushing, said sample from said tubular element with said rod.

7. A process according to claim 3 wherein said tip is removed from said pool within two seconds or less after submerging said tip.

8. A process according to claim 1 wherein said molten material is drawn into said tubular element within a period of one second or less.

9. A process according to claim 1 wherein said molten material is drawn into said tubular element with a period of one half second or less.

10. A process according to claim 1 wherein said molten material is drawn into said tubular element made of a material selected from the group consisting of carbon, graphite, graphitized carbon, carbon fibre-reinforced carbon-based materials and boron nitride.

11. A process according to claim 1 wherein said molten material is an aluminum metal and said metal is drawn into said tubular element made of graphite having a ratio of a diameter of said bore to an outer diameter of said tubular element falling in the range of 0.3–2:9.

12. A process according to claim 1 wherein said molten material is drawn into said tubular element made of a substance having a room temperature specific heat of at least 0.7 J/g K and a thermal conductivity of at least 3 W m$^{-1}$K$^{-1}$.

* * * * *